United States Patent [19]

Morf

[11] 4,318,299
[45] Mar. 9, 1982

[54] MEASURING FUNNEL FOR DETERMINING THE TENSION OF SLIVERS

[75] Inventor: Richard Morf, Uster, Switzerland

[73] Assignee: Zellweger Uster Ltd., Uster, Switzerland

[21] Appl. No.: 127,059

[22] Filed: Mar. 4, 1980

[30] Foreign Application Priority Data

Apr. 6, 1979 [CH] Switzerland .................. 3290/79

[51] Int. Cl.³ ..................... G01L 5/04; G01N 33/36
[52] U.S. Cl. .................................................. 73/160
[58] Field of Search ................. 73/160; 57/264, 265

[56] References Cited

U.S. PATENT DOCUMENTS

| 3,752,170 | 8/1973 | Morbach | 73/160 |
| 3,854,330 | 12/1974 | Wildbolz | 73/160 |
| 3,925,850 | 12/1975 | Lytton | 73/160 |
| 4,184,361 | 1/1980 | Erben | 73/160 |

Primary Examiner—S. Clement Swisher
Attorney, Agent, or Firm—Craig and Antonelli

[57] ABSTRACT

A measuring funnel for determining the tension of slivers includes a stationary component having a funnel-shaped inlet opening and a movable component. The bore for the passage of the sliver continues in the movable component, and may have a section along which it continues to taper. The passage of sliver thereby exerts a force on the movable component in the direction of its travel. This force is compensated by pneumatic or electrical means, so that the movable component takes a balanced position for every sliver cross section. These balanced positions are then converted into corresponding signals by means of electrical or pneumatic sensors, which signals are either used for measuring the absolute sliver cross section or for regulating the sliver cross section to a set value.

17 Claims, 5 Drawing Figures

MEASURING FUNNEL FOR DETERMINING THE TENSION OF SLIVERS

This invention relates in general to devices for use in the textile industry, and more particularly, to measuring funnels for determining the tension and from that the thickness of slivers.

Determining the thickness of slivers (sliver count) during operation for the purpose of obtaining a measurable variable which can be evaluated to control the sliver count is a problem which has existed for a long time, and numerous ways of solving the problem have been suggested. Thus, it has been proposed to determine the sliver count by means of electrical or optical measuring apparatus, as known from standard measuring devices (evenness testers). However, such measuring apparatus is not suitable for practical use, firstly, because it is difficult to construct such apparatus mechanically in the spatially very-restricted zones in which it is appropriate to measure the sliver count, and secondly, because they do not meet the extremely severe operational criteria of production machines. Consequently, other measuring methods, in particular, pneumatic methods, have been developed including so-called active-pneumatic and passive-pneumatic measuring systems.

Active-pneumatic measuring systems are those in which the sliver is drawn through a funnel (measuring nozzle). The air which is contained in the sliver is thereby partially driven out so as to produce a pressure which can be removed by a manometer connection opening into one side of the measuring nozzle and can be converted into a measuring signal or a control signal.

In measuring systems known as passive-pneumatic measuring systems, compressed air is admitted into a flow chamber through which the sliver passes. Variations in pressure within the flow chamber are used as a measuring signal, which variations result from the flow chamber being more or less tightly sealed off by the variable sliver cross section against the outflow of the admitted compressed air. Another measuring system of this type makes use of the frictional drag which the sliver undergoes when passing through a compressor (condenser), which is up so that it oscillates in an elastic manner, making it possible to measure the sliver on the basis of the swing span of the compressor.

Both the active-pneumatic and the passive-pneumatic measuring systems produce results which can only be used for fiber material having at least an approximately-constant fiber fineness. On the other hand, they are unreliable for fiber material having a heavily-scattered fiber fineness. Even measuring systems comprising an elastically-oscillating compressor have not been successful in practice. The reasons for this are probably to be found in mechanical difficulties in the devices themselves, in that, besides the greater mass of the compressor and the expense of the mechanism, difficulties with regard to the inflow and passage of the sliver in the compressor also prevent it from being more widely used. These difficulties include the effects of a web which runs unsteadily, static charges and changes in the pull resistance of the compressor as a result of the accumulation of dust or wax therein.

An object of the present invention is to avoid these disadvantages and to provide a measuring funnel for determining the tension of the slivers which represents a substantial and significant improvement over the known prior art.

The measuring funnel of the present invention has a number of advantages in contrast to the previous systems. One advantage is, for example, derived from the fact that the measuring funnel comprises one fixed and one movable component, the fixed component causing the sliver to be precompressed and, in particular, serving to guide the fibers. No impurities are removed at the inlet itself. Compressed air is admitted to balance the tension force of the sliver on the movable part and also serves to automatically clean the components which are displaced opposite each other as well as the hollow chamber of the funnel. By regulating the compressed air applied to the chamber of the funnel, the movable part can be set at a preselected balance point representing a given tension on the sliver. However, this balance can also be achieved by means of an electromagnetic arrangement using coils and soft iron magnets. The tension itself can be determined by detecting the position of the movable component either pneumatically or electrically and control over the thickness of the sliver is effected by generating an error signal when the movable part deviates from this balance position. The measuring funnel is also position-independent, that is to say, its installation in production machines is not restricted by requirements made for a certain position.

Various embodiments of the invention will now be described in more detail with the reference to the accompanying drawings.

Figure 1:
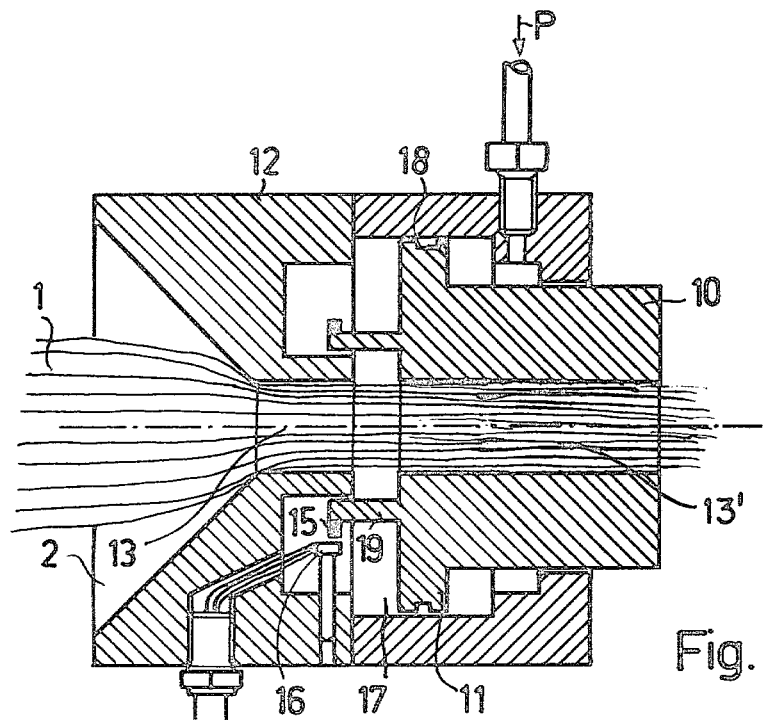
FIG. 1 is a sectional view which shows a measuring funnel comprising a magnetic-electrical positional sensor in accordance with this invention.

The measuring funnel illustrated in FIG. 1 comprises a fixed component 12 which has a funnel-shaped inlet opening 2 for the sliver 1 on the inlet side. The sliver is compressed in the opening 2 to the diameter of a continuous passage 13. A cylinder 17 is secured onto the stationary component 12 in any known way, and a movable component 10, formed as a plunger 11, is axially movable in the cylinder 17. An air gap 18 is provided between the plunger 11 and the interior wall of the cylinder 17.

The passage 13 of the stationary component 12 continues as a bore 13' in the movable component 10, in which the same diameter is at first retained. This passage formed by the bore 13' optionally may also be made to lead into a section 14 (FIGS. 2 and 3) in which its diameter tapers so that the sliver is compressed even more. In this regard, the passage may taper over a short axial length such as provided by section 14 or the taper may extend over the entire length of the passage. As a result of the compression of the sliver 1, during the travel through the passage, a force is produced which moves the movable component 10 to the right. The magnitude of this force depends on the cross section of the passing sliver.

In order to maintain the plunger 11, i.e., the movable component 10, in a balanced position, compressed air is admitted into the cylinder 17 behind the plunger 11, in the arrangement according to FIG. 1, and this compressed air pushes the plunger 11 to the left. By proportioning the pressure (P) of the applied compressed air and air gap 18 in a suitable manner, the normal position of the plunger 11 can be located approximately in the center of the cylinder 17 for a sliver of preselected cross section. When the sliver becomes thicker, the plunger 11 is displaced to the right, as seen in FIG. 1, since the tension forces are increasing. A thinner sliver produces less of a tension, so that the pressure exerted on the plunger 11 by the compressed air displaces the plunger 11 to the left, as seen in FIG. 1.

There is now the problem of measuring these displacements of the plunger 11 or of the movable component 10, and possibly of converting such movements into a proportional electrical signal for control purposes. In the embodiment of FIG. 1, this is achieved by using a standard proximity sensing device, such as a field plate 16. This is located in the operational region of a soft iron component 15. The soft iron component 15 is secured to a tube 19 protruding from the movable component 10. In this manner, the displacements of the soft iron component 15, relative to the field plate 16, are converted into electrical error signals, which are carried outside to corresponding measuring or control devices by means of wires 20. In this way, the set value of the sliver cross section can be adjusted by the choice of pressure P.

Figure 2:
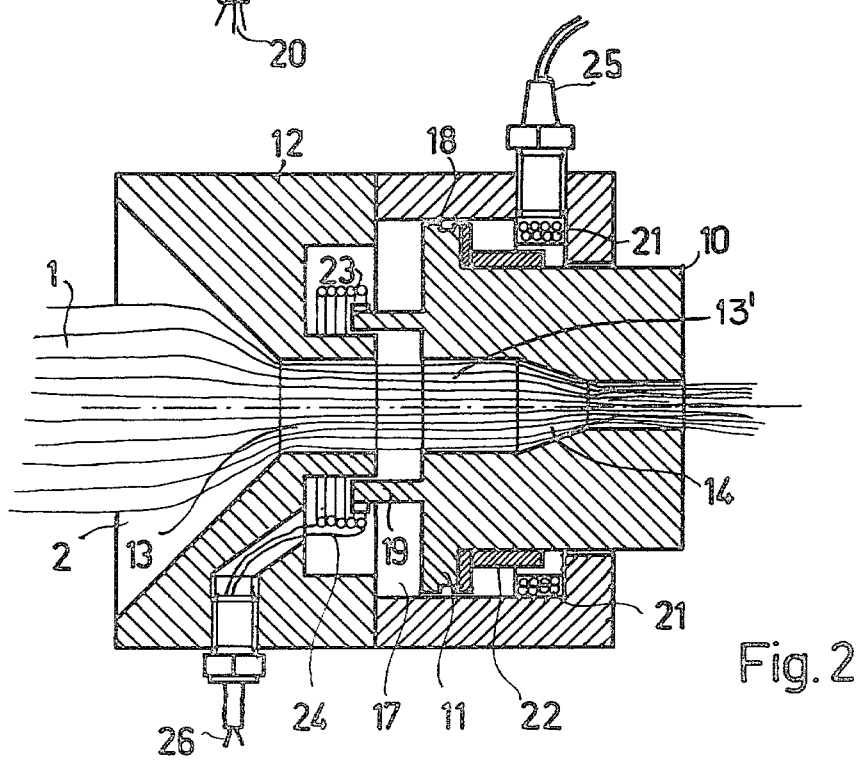
FIG. 2 is a sectional view which shows a measuring funnel forming another embodiment of this invention comprising an electromagnetic plunger drive and an inductive positional indicator.

FIG. 2 shows another embodiment of the present invention including an electromagnetic arrangment for the production of the restoring force on the movable component 10, together with an inductive determination of the position of the movable component 10 with respect to the stationary component 12. An induction current is conveyed to an induction coil 21 by leads 25. In this way a solenoid 22 which is located around the movable component 10, is energized to push the plunger 11 to the left against the tension force of the sliver. The magnitude of the repulsion or the tension which is to be generated is determined by the magnitude of the induction current.

The position of the plunger is measured by means of a soft iron ring 24 located on the tube 19. This ring moves inside a plunger type coil 25 and influences the inductive resistance of the coil. The corresponding signal generated by the coil can be taken out at the signal terminals 26 to be used for measurement and/or control.

Figure 3:
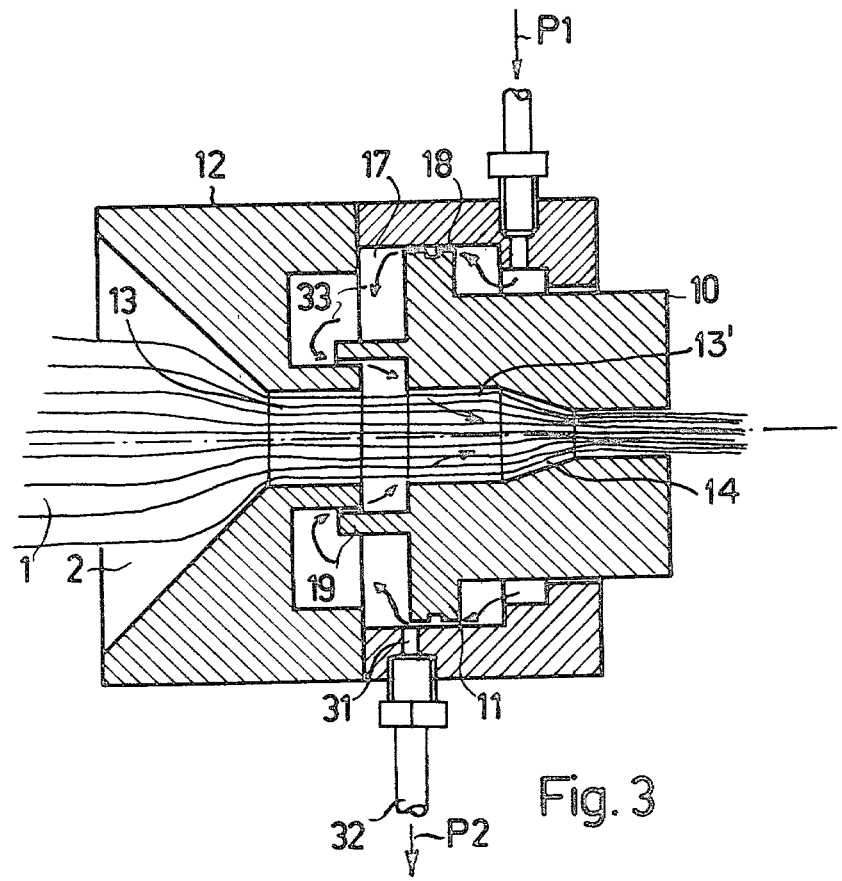
FIG. 3 is a sectional view which shows another variation of the measuring funnel of FIG. 1 including a pneumatic positional sensor.

FIG. 3 shows another embodiment of a device for pneumatic determination of the position of the plunger 11 inside the cylinder 17, which is similar to the embodiment of FIG. 1. For this purpose, at least one radial bore 31 is provided in the wall of the cylinder 17, and is at least partially covered by the plunger 11, so that the bore 31 is more or less closed according to the position of the plunger 11. In this way, corresponding pressure values P2 are produced at an air outlet opening 32, which values give an indication of the position or plunger 11 in the cylinder 17. The magnitude of the admitted compressed air P1 again provides a measurement for the set value of the sliver cross section, so that the pressure P2 represents an error value.

FIG. 3 also indicates how the cylinder 17, the air gap 18 and the chamber behind and in front of the tube 19 are kept clear of deposits of fibers, grime and other disturbing elements. For this purpose, the air flowing through the air gap 18 behind the plunger 11 (arrow 33), is arranged to penetrate into the intermediate chamber between the stationary and movable component and is carried along from there by the sliver. Consequently, the impurities which have been mentioned also take the same route before they can become attached to one of the components.

Figure 4:
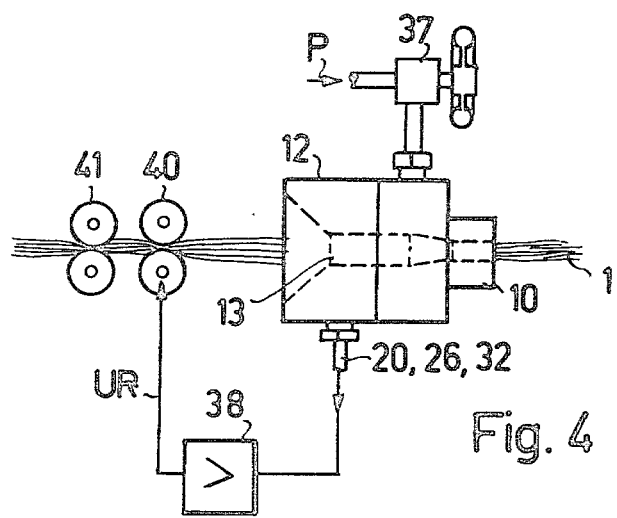
FIG. 4 is a schematic diagram which shows a measuring funnel in a control loop for comparatively moderating a fiber sliver.
Figure 5:
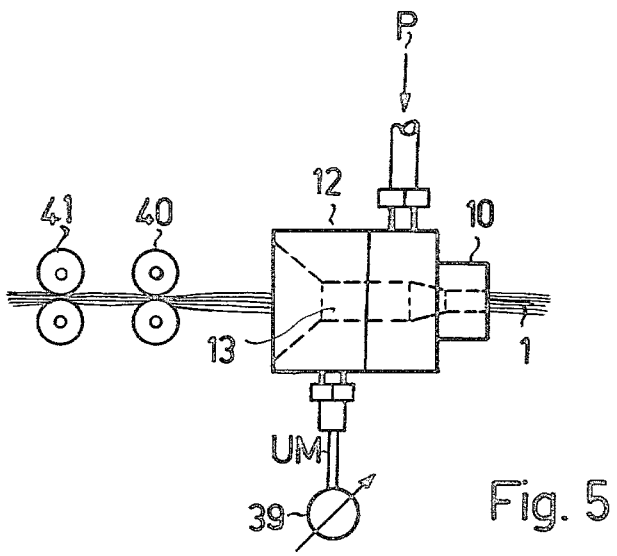
FIG. 5 is a schematic diagram which shows a measuring funnel as a measuring device for the sliver cross section.

FIGS. 4 and 5 show the measuring funnel as a control or measuring device. According to FIG. 4, which is based on the embodiment of FIG. 1, for example, the compressed air P is introduced into the measuring funnel by a control valve 37. The output to the wires 20 is transformed into a control signal UR in an amplifier 38. This control signal influences, for example, the draft between a pair of back drafting rollers 41 and a pair of front drafting rollers 40. So long as the sliver 1 has a cross section which is too large, the control signal influences the draft system 40,41 so that the draft is increased, while a too-small cross section decreases the draft and thereby increases the fiber cross section.

The arrangement of FIG. 4 is applicable in the same way to the embodiments of FIGS. 2 and 3. However, with the embodiment of FIG. 3, since the output is in the form of an air pressure signal, a diaphragm transducer or other known means must be provided to convert the pressure signal to an electrical signal which may be used to provide the control signal UR.

Finally, FIG. 5 shows the measuring funnel according to the invention as a measuring device. In this case, the output to the wires 20, or terminals 26 or air outlet opening 32 is indicated by a suitable instrument without the magnitude of the draft being affected in the draft system 40,41. However, it should also be apparent that such a measuring instrument could be added to the arrangement of FIG. 4 to provide both measurement and control.

While I have shown and described several embodiments in accordance with the present invention, it is understood that the invention is not limited thereto but is susceptible of numerous changes and modifications as are known to those of ordinary skill in the art, and I therefore do not wish to be limited to the details shown and described herein but intend to cover all such changes and modifications as are obvious to one skilled in the art.

What is claimed is:

1. A measuring funnel for determining the tension of fiber slivers, comprising a stationary component having a first bore therein through which said fiber sliver passes and a movable component which moves in a translational manner with respect to the stationary component, the movable component having a second bore therein coextensive with said first bore and being arranged to be displaced from a preselected position by the passage of the fiber sliver through said second bore, and balance means for applying a predetermined force to said movable component to counteract the displacement thereof by a fiber sliver of selected cross section.

2. A measuring funnel according to claim 1, further including means for detecting the position of the movable component with respect to the stationary component.

3. A measuring funnel according to claim 1, wherein said second bore comprises a continuous passage, which tapers in the direction of travel of the fiber sliver at least along one part of its length.

4. A measuring funnel according to claim 1, wherein the movable component comprises a plunger movable in an axial direction within a stationary cylinder.

5. A measuring funnel according to claim 1, wherein said balance means includes a fluid pressure source and means to apply fluid pressure to the movable component, which counteracts its displacement by the fiber sliver.

6. A measuring funnel according to claim 5, further including means for adjusting the selected value of the sliver cross section by controlling the magnitude of the applied fluid pressure.

7. A measuring funnel according to claim 1, wherein said balance means includes electromagnetic force producing means for producing an electromagnetic force which counteracts the displacement of said movable component.

8. A measuring funnel according to claim 7, wherein said electromagnetic force producing means includes a plunger type coil and a soft iron ring.

9. A measuring funnel according to claim 8, wherein said electromagnetic force producing means includes means for adjusting the selected value of the sliver cross section by adjusting the magnitude of the current flowing through said plunger type coil.

10. A measuring funnel according to claim 1, further including means for generating a control signal representing the positional deviations of the movable component from said preselected position which is related to the selected value of the sliver cross section and means responsive to said control signal for controlling the actual sliver cross section so as to maintain said selected value.

11. A measuring funnel according to claims 1, 2 or 3, further including means responsive to the position of the movable component which is adjusted by the pull of the fiber sliver for generating a measuring signal representing the cross section of the fiber sliver.

12. A measuring funnel according to claim 11, wherein said means responsive to the position of the movable component comprises an electrical detector.

13. A measuring funnel according to claim 12, wherein said electrical detector includes a soft iron component which acts on a fieldplate.

14. A measuring funnel according to claim 12, wherein said electrical detector includes an inductor, the magnitude of the inductance of which can be changed by the position of the movable component.

15. A measuring funnel according to claim 1, further including pneumatic detector means for detecting the position of the movable component which is adjusted by the pull of the sliver.

16. A measuring funnel according to claims 1 or 15, wherein a cylinder is provided in association with said stationary component with at least one radial bore being provided therein, said movable component comprising a plunger arranged within said cylinder so as to at least partially cover said radial bore according to its position, and further including means connected to the radial bore for determining the magnitude or proportion of the part of the bore which is not covered by the plunger.

17. A measuring funnel according to claim 1, wherein an air gap is provided between the movable component which is formed as a plunger and the stationary component acting as a cylinder, through which gap at least a part of the admitted compressed air flows into the chamber behind the plunger and thereby prevents deposits of grime.

* * * * *